(12) United States Patent
Shmueli

(10) Patent No.: US 10,660,681 B2
(45) Date of Patent: May 26, 2020

(54) UNIVERSAL IMPLANT-TO-BONE FIXATION SYSTEM

(71) Applicant: RayCont Ltd., Yad Natan (IL)

(72) Inventor: Gad Shmueli, Yad Nathan (IL)

(73) Assignee: RAYCONT LTD., Yad Natan (IL)

( * ) Notice: Subject to any disclaimer, the term of this patent is extended or adjusted under 35 U.S.C. 154(b) by 475 days.

(21) Appl. No.: 15/314,533

(22) PCT Filed: May 10, 2015

(86) PCT No.: PCT/IL2015/050486
§ 371 (c)(1),
(2) Date: Nov. 29, 2016

(87) PCT Pub. No.: WO2015/186123
PCT Pub. Date: Dec. 10, 2015

(65) Prior Publication Data
US 2017/0196611 A1    Jul. 13, 2017

Related U.S. Application Data

(60) Provisional application No. 62/006,186, filed on Jun. 1, 2014.

(51) Int. Cl.
*A61B 17/86* (2006.01)
(52) U.S. Cl.
CPC ........ *A61B 17/8625* (2013.01); *A61B 17/861* (2013.01); *A61B 17/862* (2013.01); *A61B 17/8605* (2013.01); *A61B 17/8615* (2013.01)

(58) Field of Classification Search
CPC ............ A61B 17/8625; A61B 17/8605; A61B 17/861; A61B 17/8615; A61B 17/862; F16B 25/00; F16B 25/0021; F16B 25/052
(Continued)

(56) References Cited

U.S. PATENT DOCUMENTS

| 45,133 | A | * | 11/1864 | Bonwill | ............ F16B 25/0015 |
| | | | | | 411/421 |
| 1,933,332 | A | * | 10/1933 | May | ........................ F16B 39/30 |
| | | | | | 411/418 |

(Continued)

FOREIGN PATENT DOCUMENTS

| CH | 693733 | 1/2004 |
| WO | WO 2015/186123 | 12/2015 |

OTHER PUBLICATIONS

International Preliminary Report on Patentability dated Dec. 15, 2016 From the International Bureau of WIPO Re. Application No. PCT/IL2015/050486. (14 Pages).
(Continued)

*Primary Examiner* — Jessica Weiss
(74) *Attorney, Agent, or Firm* — The Roy Gross Law Firm, LLC; Roy Gross

(57) ABSTRACT

A Universal implant-to-bone anchoring system including an anchor having a shaft terminated at one end by a head and one or more tins, generally planar and having two surfaces, portions of which come together at a free edge, and attached to the shaft and angled about a minor radius thereof along an imaginary helix and an inserter operative to be attached to the head of the anchor and having one or more ports operative to accommodate an anchor driving tool.

11 Claims, 6 Drawing Sheets

(58) Field of Classification Search
USPC .................. 606/300–321; 411/420–421, 417
See application file for complete search history.

(56) References Cited

U.S. PATENT DOCUMENTS

| | | | | |
|---|---|---|---|---|
| 2,093,172 | A * | 9/1937 | Olson | F16B 25/0021 411/420 |
| 2,269,708 | A * | 1/1942 | Dickson | F16B 15/06 24/114.05 |
| 3,426,642 | A * | 2/1969 | Phipard, Jr. | F16B 25/0021 411/417 |
| 3,987,698 | A * | 10/1976 | Rabe | F16B 15/06 411/455 |
| 4,177,524 | A * | 12/1979 | Grell | A61L 27/32 606/86 R |
| 4,425,066 | A * | 1/1984 | Kollmann | F16B 25/0031 411/387.4 |
| 4,466,314 | A | 8/1984 | Rich | |
| 4,653,486 | A * | 3/1987 | Coker | A61B 17/68 606/65 |
| 4,815,909 | A * | 3/1989 | Simons | B21H 3/027 411/392 |
| 5,110,245 | A * | 5/1992 | Hiroyuki | F16B 25/0015 411/417 |
| 5,282,863 | A * | 2/1994 | Burton | A61B 17/7007 606/254 |
| 5,716,358 | A | 2/1998 | Ochoa et al. | |
| 6,022,177 | A * | 2/2000 | Hofer | F16B 5/0275 411/399 |
| 6,428,317 | B1 * | 8/2002 | Abel | B21F 45/008 433/102 |
| 6,676,352 | B2 * | 1/2004 | Chen-Chi | F16B 37/125 411/178 |
| 7,156,600 | B2 * | 1/2007 | Panasik | B21H 3/02 411/308 |
| 8,292,932 | B2 * | 10/2012 | Matthis | A61B 17/864 606/300 |
| 8,635,894 | B2 * | 1/2014 | Christ | B21H 3/02 72/88 |
| 2004/0253076 | A1 * | 12/2004 | French | F16B 15/06 411/417 |
| 2005/0175432 | A1 | 8/2005 | Su | |
| 2005/0187555 | A1 * | 8/2005 | Biedermann | A61B 17/68 606/62 |
| 2006/0285940 | A1 * | 12/2006 | Walther | F16B 25/0026 411/421 |
| 2012/0109216 | A1 | 5/2012 | Austin et al. | |
| 2013/0089835 | A1 | 4/2013 | Jensen | |
| 2013/0253649 | A1 * | 9/2013 | Davis | A61B 17/1615 623/17.16 |
| 2013/0337410 | A1 * | 12/2013 | Ten Bruggenkate | A61B 17/8625 433/174 |

OTHER PUBLICATIONS

International Search Report and the Written Opinion dated Oct. 7, 2015 From the International Searching Authority Re. Application No. PCT/IL2015/050486.

* cited by examiner

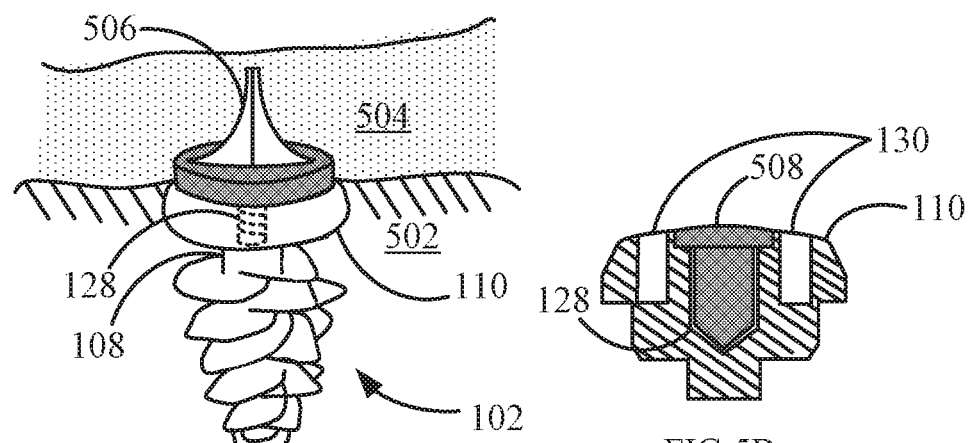
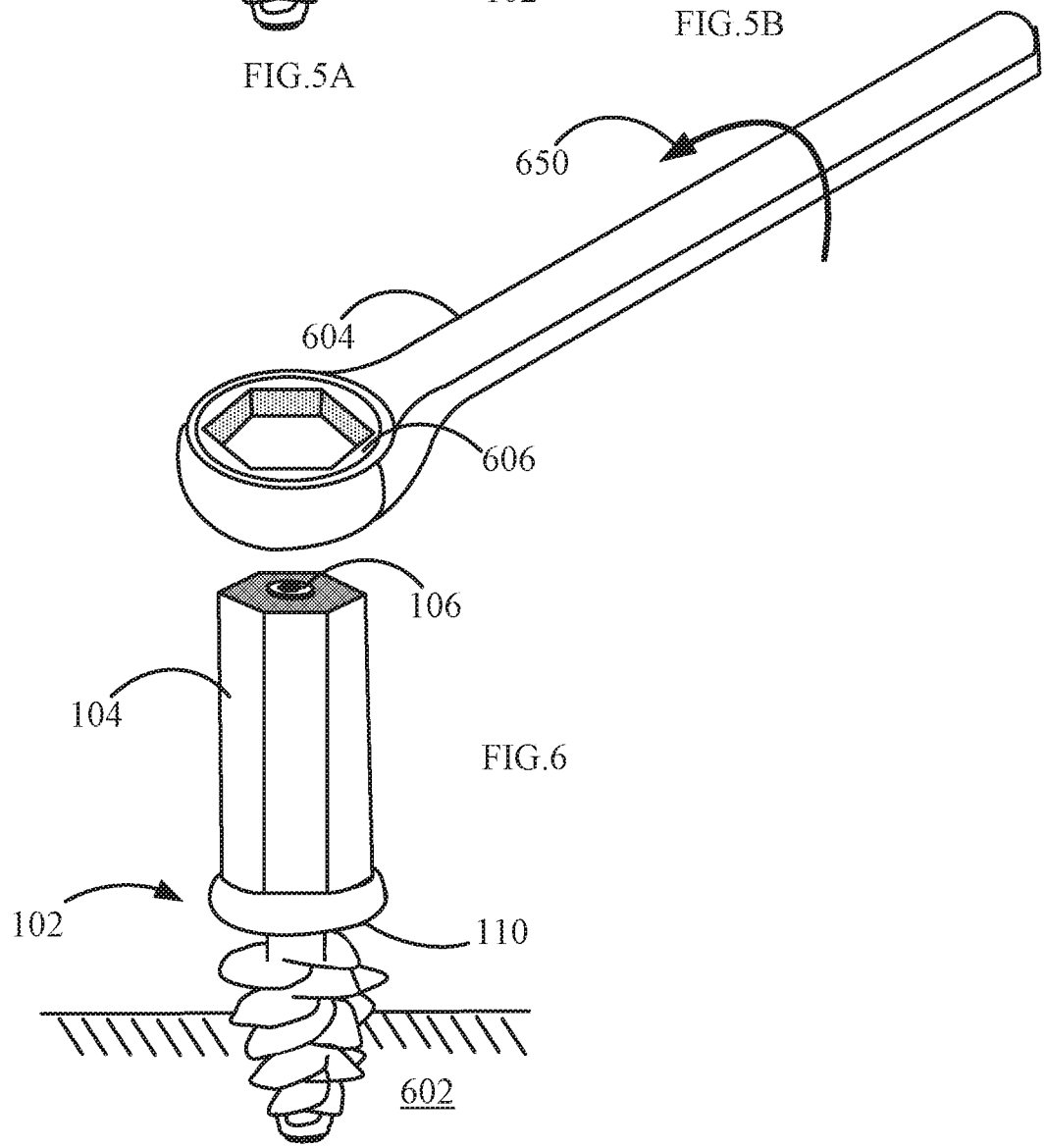

UNIVERSAL IMPLANT-TO-BONE FIXATION SYSTEM

RELATED APPLICATIONS

This application is a National Phase of PCT Patent Application No. PCT/IL2015/050486 having International filing date of May 10, 2015, which claims the benefit of priority under 35 USC § 119(e) of U.S. Provisional Patent Application Ser. No. 62/006,186 filed on Jun. 1, 2014. The contents of the above applications are all incorporated by reference as if fully set forth herein in their entirety.

TECHNOLOGY FIELD

The system relates to implant-to-bone fixation systems and in particular to universal systems for fixation of implants to bone.

BACKGROUND

In orthopedic and orthodontic procedures the need often arises to fix an implant to bone. The most common method for such fixation is carried out by using various types of pins and/or screws commonly designed for a specific orthopedic or orthodontic procedure.

One such procedure, for example, would be to fix joint articulation surface implants to the underlying bone as part of an arthroplasty procedure such as described in US Patent Application Publication No. 2009\0222103. Another example for fixation of a bone plate to a bone using screws is described in U.S. Pat. No. 5,578,034. U.S. Pat. No. 3,466,478 discloses an anchor screw for fixating an orthodontic prosthesis to the jaw bone.

In arthroplasty, it is very important for the implant to remain firmly attached to the underlying bone over time. Fixation of such implants to bone have originally employed cement. Later cementless fixation techniques, mainly by employing screws and pins have been developed.

In many cases, however, fixation devices such as screws, pins or similar keeping implants such as arthroplasty implants in place are embedded in the bone at locations commonly subject to high stress such as compression and shearing forces, bending forces, torque or a combination of all. In arthroplasty, for example, the bone joint articulation surfaces can be such a location. An articulating joint by definition is subjected to high stress such as forces of compression and shearing resulting from the shift of the load-bearing articulating surfaces during movement of the articulating bones such as during walking.

Another such location can be the jaw bone in which an orthodontic insert can be placed in a jaw bone supporting an implant. Here too, the orthodontic insert must withstand significant excessive compressive and bending forces transferred thereto from the implant during mastication.

The stress to which the implants are subjected many times impacts the bone screw or pin by bringing about failure of the fixation device. Such failure commonly exhibits itself in the form of loosening, device fatigue and axial pull-out of the device, i.e., axial forces acting, for example on a screw and translated into rotational forces that cause the device to unscrew and loosen bringing about irreversible loss of the bone-implant interface. Since the thread created in the bone cortex by the commonly used screws is relatively shallow, in some cases the bony thread itself may strip and the fixating device can lose its holding power or grip.

Several attempts have been made to overcome the above described failures. U.S. Pat. No. 6,575,975 discloses one example of a fixation device comprising a bushing having a locking screw that is threaded through the head of the bushing expanding the radial walls of the head and locking the bushing in place.

U.S. Pat. No. 5,716,358 discloses an orthopedic bone screw having directional asymmetry and asymmetrical surface roughness provided by a plurality of oriented microstructures on the surface.

Another contributing factor to fixation devices premature loosening and failure is the shoulder of the fixation device such as a bone plate lag screw. Lag screws are commonly designed to slip along the shoulder of screw hole in a bone plate hence the shoulders of the lag screw are rounded. Rounded shoulders allow for pendulous movement ("rocking") of the bone over time in response to the various forces of stress discussed above. This pendulous movement eventually leads to loosening of the screw or similar fixation device leading to failure.

Failure may not necessarily be mechanical in nature. Bringing two dissimilar conducting materials, such as metals, in contact with each other leads to an electrochemical potential difference between them and a development of galvanic corrosion. Aggressive corrosion resulting from an electrical circuit established between the two different metals one of which becomes an anode while the other—a cathode. Common sense would dictate not using multiple metals in an orthopedic implant.

In most cases, the fixation of an implant to bone is expected to be permanent or at least long-term. Unfortunately, this goal often remains unfulfilled for the reasons disclosed above.

Since the types of stress to which the fixation device can be subjected might vary in nature from location to location, oftentimes the proposed fixation devices are designed in an attempt to overcome fixation device failures in a specific location. Such designs require the orthopedic surgeon, dentist or medical institution to stock a variety of types of fixation devices which can become quite expensive. A single type universal fixation device that can be scaled up or down to various sizes suitable for various orthopedic as well as orthodontic procedures could provide a solution to overcome such deficiencies and bring about a reduction in manufacturing costs as well as expenses for the surgeon, dentist or medical institution.

SUMMARY

The instant patent application discloses a universal system for fixation of implants to bone. The universal system is designed to provide permanent fixation of inserts to bone, implants such as those employed in arthroplasty, carpal bone orthopedic procedures, long bone procedures, tendon and ligament repair as well as in orthodontic procedures.

There is therefore provided a universal implant-to-bone anchoring system including an anchor comprising a shaft terminated at one end by a head having a shoulder and one or more fins, generally planar and having a tapered leading edge and a tapered trailing edge, attached to the shaft and angled along an imaginary thread. The system also can include an inserter operative to be attached to the head of the anchor and having two or more ports operative to accommodate an anchor driving tool. The universal system can also include a dedicated drill guide operative to assure a snug fit between the shoulder of the anchor head and a screw hole on an implant when the shoulder is accommodated in the screw hole.

The fins are arranged on the shaft so that no fin is positioned directly over an adjacent fin.

In another example, the fins are arranged on the shaft so that at least one fin contacts both the head and the shaft of the anchor.

The universal implant-to-bone anchoring system structure, mainly the arrangement of the fins on the anchor shaft is designed so that to stimulate osseous integration in surrounding bone tissue so that to firmly and tightly embed the system anchor in healed bony tissue so that to prevent undesired loosening and axial pull-out of the anchor.

In yet another example, the anchor can also be fully or partially can be coated with a micro-granular layer of titanium alloy to further stimulate bone growth, increasing surface friction and limiting its movement after anchoring.

Universal implant-to-bone anchoring system is designed so that it can be scaled up or down to various sizes suitable for various orthopedic as well as orthodontic procedures.

In still another example, the system can be designed for procedures requiring compression of a fracture being repaired, such as for example, carpal bone surgery. In such a configuration the fins can be attached to only a portion of the anchor shaft leaving a portion of the shaft adjacent to head bare, with no fins attached.

The universal system for fixation of implants to bone can replace mutatis mutandis most implant-to-bone fixation devices such as screws, threaded pins and non-threaded pins and any other similar devices.

BRIEF DESCRIPTION OF THE FIGURES

FIGS. 5A and 5B are perspective and cross-section view simplified illustrations of an implementation of a universal system for fixation of implants to bone in accordance with yet another example;

FIG. 6 is a perspective view simplified illustration of an implementation of a driving tool for a universal system for fixation of implants to bone in accordance with still another example.

DETAILED DESCRIPTION

Figure 1A:
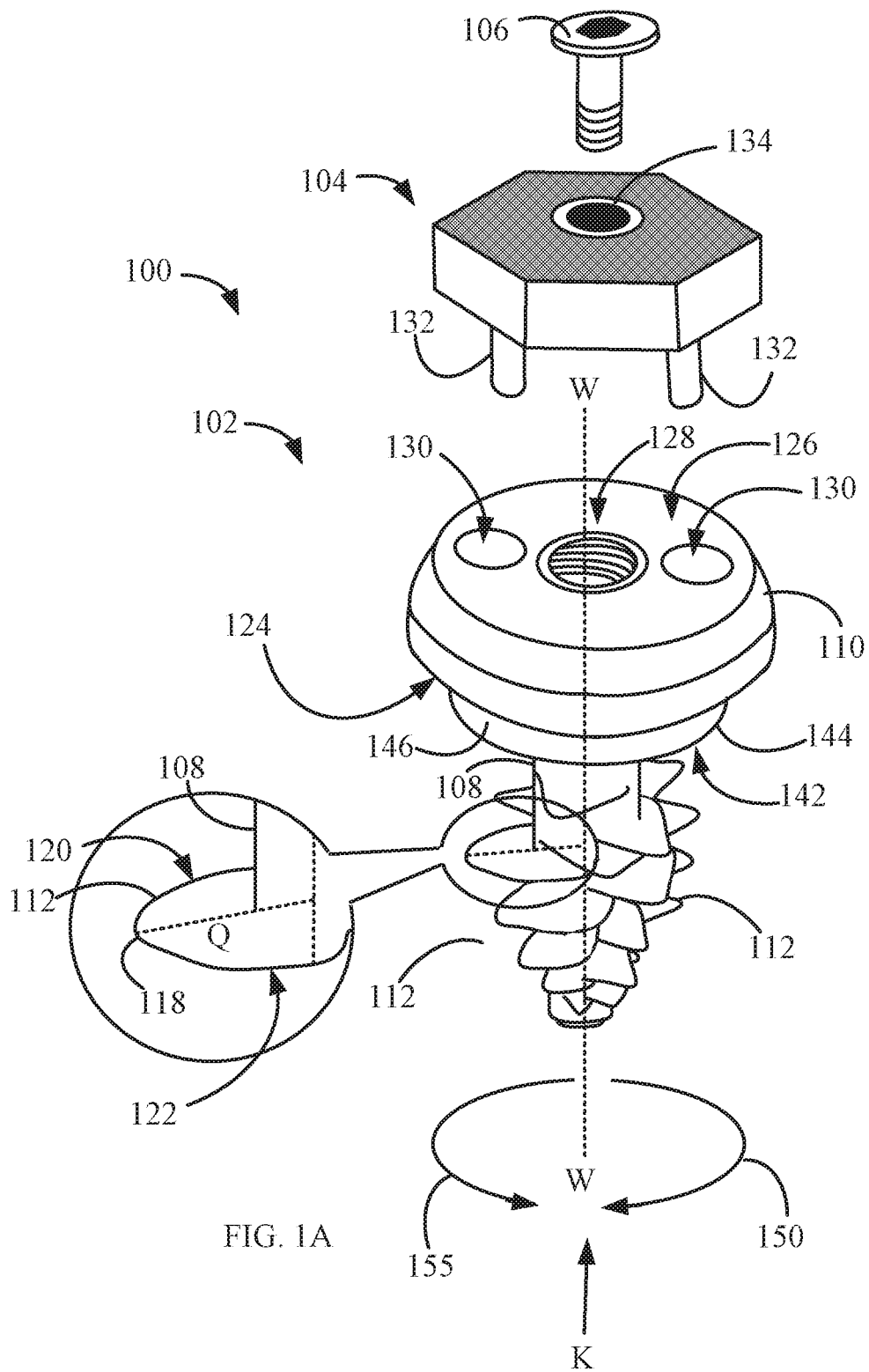
FIGS. 1A, 1B, 1C and 1D are a perspective view and elevated lateral view simplified illustrations of an example of a universal system for fixation of implants to bone.

The term "Major Radius" as disclosed in this application refers to the largest radius (outside circumference) of a fin as measured from a central longitudinal axis (X) of the anchor.

The term "Pitch" as disclosed in this application refers to the distance from a point on a tin to a corresponding point on an adjacent fin measured along parallel axes perpendicular to the central longitudinal axis (X) of the anchor.

The term "Helix Angle" as disclosed in this application refers to the constant angle at which a helix cuts the elements of an anchor, measured relative to an axis perpendicular to the anchor longitudinal central axis (X) of the anchor and marked as (a).

The term "Fin Crest" or "Crest of Fin" as disclosed in this application refers to the free edge of the fin corresponding to the major radius (outside circumference) of the fin.

The term "Fin Root" or "Root of Fin" as disclosed in this application refers to the edge of the fin that is attached to the shaft of the anchor.

The term "Minor Radius" as disclosed in the current application refers to the shortest distance between the fin root and the fin crest.

Reference is made to FIGS. 1A, 1B, 1C and 1D, together referred to as FIG. 1, which are perspective and elevated lateral views of a universal system for fixation of implants to bone in accordance with an example. System 100 can include an anchor 102 including a shaft 108 terminated at one end by a head 110 and including one or more fins 112, an inserter 104 including one or more anchor 102 driving pins 132 and a locking screw 106. Universal system 100 can be scaled up or down in size to fit various orthopedic procedures such as, for example, long bone surgery (e.g., femoral fractures, tibial fractures, humeral fractures, etc.), various joint procedures (e.g., arthroplasty) and for small bone surgery (e.g., carpal bone fracture fixations) as well as for orthodontic procedures in which system 100 can be scaled down to fit in a jaw bone and accommodate, for example, an orthodontic abutment (506, FIG. 5A).

Anchor 102 can be made of any suitable biocompatible material such as, for example, stainless steel, cobalt-chrome molybdenum (CoCrMo) alloy or titanium alloy. Anchor 102 can be made of the same material of which the implant to be fixed is made to prevent the development of electrical micro-currents and galvanic corrosion that can bring about local sterile inflammation of the bone. Since the material most commonly used for implants and currently used arthroplasty implants as well is titanium alloy, anchor 102 can be made of the same titanium alloy as the implant.

Another advantage in use of titanium alloy is in that it is non-allergenic. Most currently used fixation devices, such as bone screws are made of stainless steel that often contains nickel and chrome that can be allergenic.

As discussed in several articles such as, for example, *In Vivo Evaluation of Immediately Loaded Stainless Steel and Titanium Orthodontic Screws in a Growing Bone*/Kerstin Gritsch mail et al., Oct. 4,2013/DOI: 10.137/'journal-.pone.0076223; *Long-term biocompatibility and osseointegration of EBMd solid and porous Ti alloy—Experimental Studies in Sheep*/A. Palmquist et al./*J. of Biomaterial Applications* 0(0) 1-14), Titanium alloy stimulates a high degree of osseointegration (i.e., direct structural and functional connection between living bone and the surface of an artificial implant) when compared to other materials.

Studies also show that micro-granularity or porosity of the implant surface further stimulates osseointegration. Hence and as shown in FIG. 1B, at least portion 140 of the surface of anchor 102 can be coated with a micro-granular layer of titanium alloy so that to further stimulate bone growth in bone surrounding anchor 102, increasing surface friction and limiting its movement after anchoring.

Additionally and optionally, anchor 102 can be made of a biocompatible polymer such as used in fixation devices for tendon repair surgery. Where applicable, anchor 102 can also be manufactured by rapid prototyping technology.

Referring back to FIG. 1 head 110 can include a first surface 124 facing shaft 108 and a second surface 126 on the opposite side of head 110 facing away from shaft 108. Surface 126 can include a centrally located threaded bore 128 shaped to accommodate locking screw 106 and two or more smooth-walled bores 130 operative to accommodate driving pins 132 of inserter 104. Optionally, bores 130 can be also threaded.

A common contributing factor to fixation devices premature loosening and failure is the head structure of the fixation device such as, for example, a bone plate lag screw. Lag screws are commonly designed to slip along an angled wall of a screw hole in a bone plate. Hence the shoulders of the lag screw are rounded. Rounded shoulders allow for pendulous movement ("rocking") of the bone screw over time in response to the various forces of stress discussed above. This pendulous movement eventually leads to loosening of the screw or similar fixation device leading to fixation failure.

Head 110 can also include a shoulder 144 commonly but not necessarily cylindrical in shape and having one or more walls 146 parallel to the central axis (X) of shaft 108, attached to first surface 124 and bordering a base 142, which in turn is attached to shaft 108. A bevel 150 is located at the angle of attachment of wall 146 to base 142. Shoulder 144 dimensions can be such so that shoulder 144 can be snugly accommodated in screw hole 752 of an implant 750 when anchor 102 is fully inserted and secured in place, as illustrated in FIG. 7C.

Referring once again to FIG. 1A, head 110 can be significantly larger than shaft 108 so that to provide surface 124 and base 142 with sufficient surface area to urge an implant (e.g., 302, FIG. 3) against the bone when anchor 102 is secured in place in its final position. The diameter of head 108 can be the same as the twice the largest major radius of fins 112, larger or smaller.

Figure 1B:
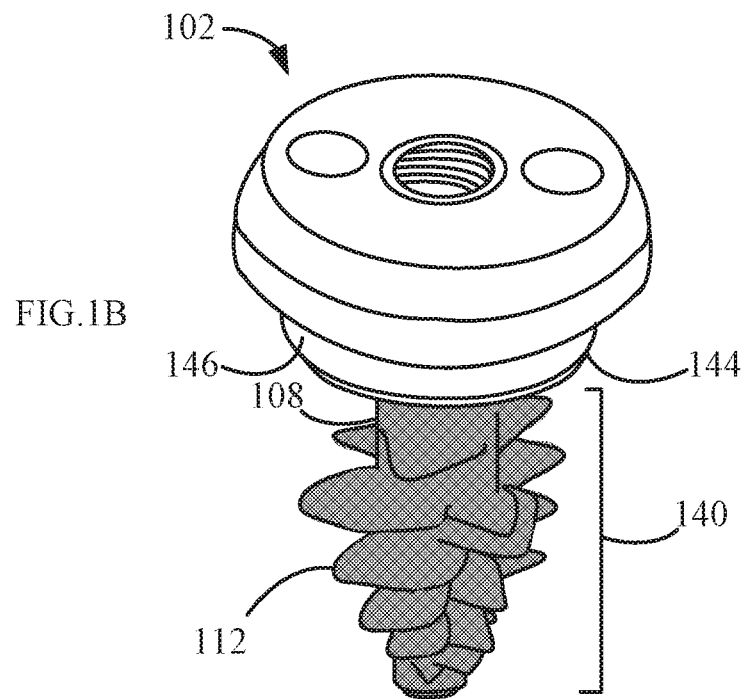
Figure 1C:
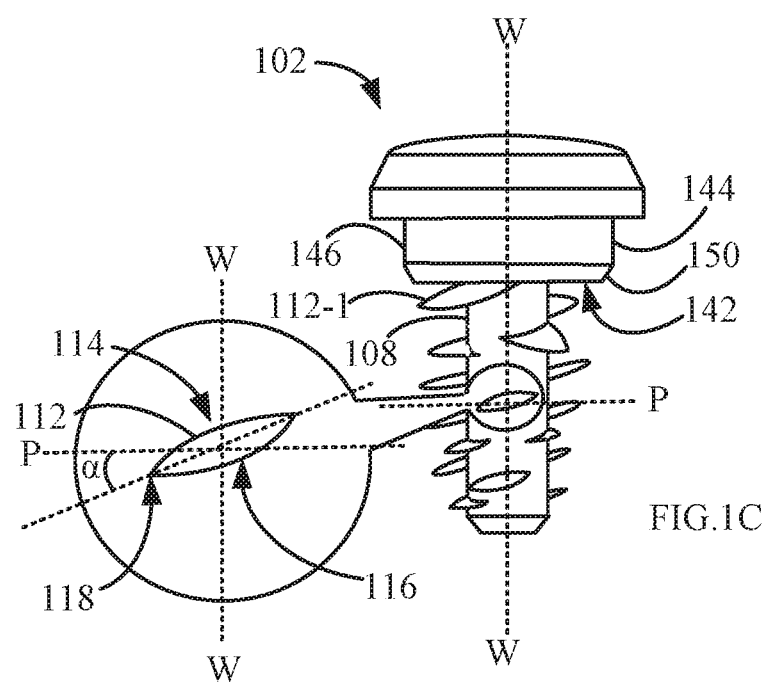

As shown in FIG. 1C, one or more fins 112 attached to shaft 108 can be generally planar, having a first surface 114 and a second surface 116 portions of which can come together at a free edge 118. Surfaces 114 and 116 can be flat, convex or concave. Fins 112 can be arranged along an imaginary helix (not shown) winding about a central longitudinal axis (W) of anchor 102. Alternatively and optionally, fins 112 can be arranged along an imaginary double helix (not shown) winding about central longitudinal axis (W).

The minor radius of each one of fins 112 can decrease in size the farther from the head the location of fin 112 along shaft 108. That is the minor radius of fin 112 closest to head 110 is the largest in size whereas the minor radius of fin 112 farthest from head 110 is the smallest in size. This configuration allows anchor 102 fins 112 to be self-tapping negating the need for a tapping device prior to use as commonly required in commonly used fixation devices such as screws. Optionally, shaft 108 can end at a sharp, longitudinally grooved tip (not shown) so that to also be self-tapping and operative to deepen a pre-drilled preparation bore should the preparation bore not be sufficiently deep.

Surfaces 114 and 116 can be angled about a major radius (Q) extending outwards from central longitudinal axis "W", at an helix angle (a) (FIG. 1C), relative to a plane represented in FIG. 1C by an axis Perpendicular to axis (W). Helix angle (a) can depend on the pitch between adjacent fins and the radius of anchor 102 shaft 108. Fins 112 can also be arranged at a suitable predetermined pitch so that when anchor 102 is rotated against cortical bone, one or more fins 112 can cut their way through the cortical bone axially driving shaft 108 into and along a pre-drilled bore in the cortical bone making anchor 102 a self-tapping device.

Additionally and as will be explained in greater detail below, fins 112 can also be arranged such that when anchor 102 is fully anchored and secured in bone at least one fin 112 remains embedded in cortical bone.

The surface area of at least one of surfaces 114 and 116 of a fin 112 can be the same as the surface area of a cross-section of shaft 108 at the level of the same fin 112. Alternatively and optionally, at least one of surfaces 114 and 116 of a fin 112 can have a surface area between 1.5 times and the same as the surface area of a cross section of shaft 108 at the level of the same fin 112. Alternatively and optionally, at least one of surfaces 114 and 116 of a fin 112 can have a surface area 1.5 times and greater than the surface area of a cross-section of shaft 108 at the level of the same fin 112. Commonly the surface area of the sum projections of any three adjacent fins 112 can be between 2 and 3 times the largest surface area of any cross-section of shaft 108 at any level of shaft 108. More commonly, the surface area of the sum projections of any three adjacent fins 112 can be 3 times and greater than the largest surface area of any cross-section of shaft 108 at any level of shaft 108.

Commonly the maximum diameter of fin 112 can be 1.5 to 1.7 times that of the diameter of shaft 108. More commonly the maximum diameter of fin 112 can be 1.7 times or greater that of the diameter of shaft 108.

When anchor 102 is rotated in a clockwise direction about central longitudinal axis (W) of shaft 108, as indicated by an arrow designated reference numeral 150, a portion 120 of free edge 118 can become a leading edge and a portion 122 of free edge 118 can become a trailing edge. When the direction of rotation of anchor 102 is reversed and becomes counter-clockwise, as indicated by an arrow designated reference numeral 155, portion 122 of free edge 118 can become the leading edge and portion 120 of free edge 118 can become the trailing edge. This design, in which both portions 120 and 122 are symmetrically tapered provides anchor 102 with rotational symmetry. Optionally, portions 120 and 122 can be asymmetrically tapered.

Free edge 118 can be a tapered edge uniformly tapered throughout its length or have tapered portions such as, for example portions 120 and 122 to provide one or more sharp cutting edges. The degree of taper applied to free edge 118 portions 120 and 122 can differ between portions 120 and 122 so that the level of torque applied to anchor 102 during counter-clockwise rotation (i.e., anchor 102 extraction) is greater than the level of torque applied to anchor 102 at the time of insertion as will be described in greater detail below. Optionally, free edge 118 can have a rounded or beveled crosssection or have a cross section in any applicable geometric form.

As described above, the root of fins 112 can be attached to shaft 108 along an imaginary single or double helix. Commonly each fin 112 can be attached along less than half of the circumference of shaft 108. More commonly, each fin can be attached along between one third and one half of the circumference of shaft 108 and most commonly each fin can be attached along one third or less of the circumference of shaft 108.

Fins 112 can be arranged about shaft 108 and along the imaginary helix or double helix so that there is no more than one fin 112 for each full circumference of the shaft at the level of the fin or per one full rotation of the helix (i.e., one 360 degree rotation). However, and as illustrated in FIG. 2, which is a simplified illustration of anchor 102 as viewed from a direction indicated by arrow (K) (FIG. 1), fins 112 can be arranged in such a fashion that a portion 202 of a projection 212 of one fin 112 at least partially overlaps a portion 202 of a projection 212 of at least one adjacent fin 112. Commonly, Fins 112 are arranged so than no one projection 202 of a fin 112 completely or fully overlaps a projection 202 of an adjacent fin 112. In other words, fins 112 can be arranged such that no one fin 112 is placed directly above or under an adjacent fin 112.

Fins 112 can also be arranged such that at least one fin or a portion thereof remains embedded in cortical bone once anchor 102 is fully embedded and secured in its final position in bone. This further enhances long term stability and security of anchor 102 in situ. Cortical bone thickness can vary but in most cases remains below 5 mm in thickness. Mandibular and maxillary cortical bone thickness in most cases is below 2 mm. Hence, anchor 102 designed for most orthopedic procedures, can include one or more fins 112 positioned along shaft 108 at a distance no greater than 5 mm from shoulder 144 base 142 of head 110. Anchor 102 designed for most orthodontic procedures, can include one or more fins 112 positioned along shaft 108 at a distance no greater than 2 mm from shoulder 144 base 142 of head 110. In some examples, a root of one fin 112-1 (FIG. 1C) can contact both base 142 of head 110 shoulder 144 and shaft 108.

Figure 1D:
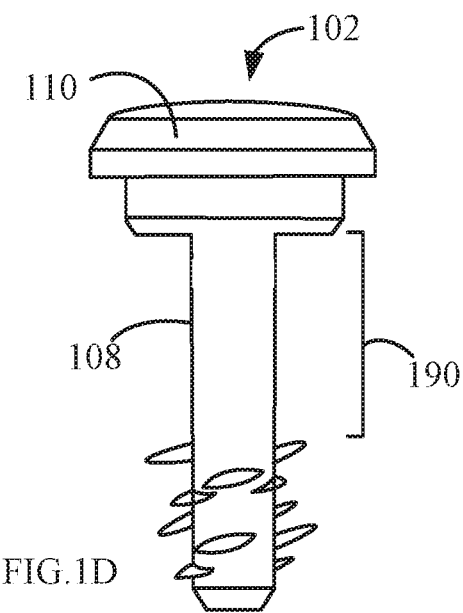
Figure 2:
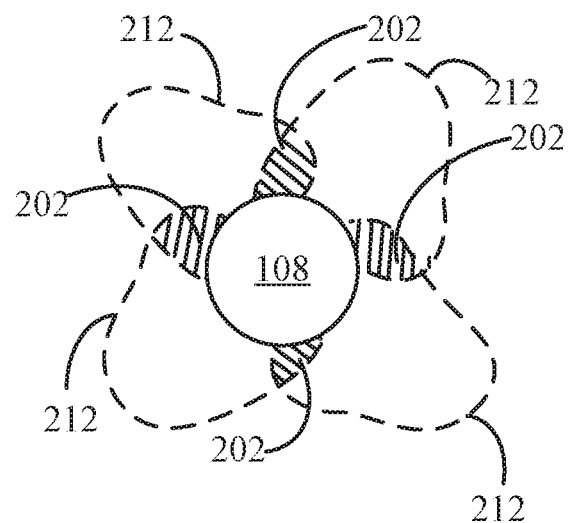
FIG. 2 is a perspective view simplified illustration of a universal system for fixation of implants to bone in accordance with yet another example.

Alternatively and optionally and as depicted in FIG. 1D, fins 112 can be attached to only a portion of shaft 108 leaving a finless portion 190 of shaft 108 between head 110 and the fin 112 closest to the head, with no fins attached. Commonly, finless portion 190 could extend over one third of the total length of shaft 108. More commonly, finless portion 190 could extend over one half of the total length of shaft 108 and most commonly finless portion 190 can extend over two thirds of the total length of shaft 108. Such a configuration renders anchor 112 a bone fracture compression fixation anchor that can be employed to replace commonly used lag screws in applicable procedures in which compression of the fracture being repaired is desired such as for example, carpal bone surgery and femoral neck fractures fixation.

It will be appreciated by persons skilled in the art that universal system 100 for fixation of implants to bone can replace mutatis mutandis most implant-to-bone fixation devices such as screws, threaded pins and non-threaded pins and any other similar devices.

Optionally, the pitch between fins 112 can also be designed in accordance with cortical bone thickness. For example, anchor 102 designed for orthodontic procedures can have a smaller designed pitch relative to the pitch designed for an anchor 112 intended for arthroplasty procedures.

Head 110 can be generally planar having a first surface 124 and a second surface 126 and can include a centrally located threaded bore 128 in surface 126 shaped to accommodate locking screw 106 and two or more smooth-walled bores 130 operative to accommodate driving pins 132 of inserter 104.

In a scaled down example, shown in FIG. 5, which is an example of implementation of anchor 102 for orthodontic use, threaded bore 128 can be designed to accommodate an orthodontic abutment 506.

Referring once again to FIG. 1, Head 110 can be significantly larger than shaft 108 so that to provide surface 128 with sufficient surface area to urge an implant (302, FIG. 3) against the cortical bone when anchor 102 is secured in place in its final position. The diameter of head 108 can be the same as the largest diameter of the sum diameter of the fins 112 or smaller.

As will be explained in greater detail below, the design of system 100 fins 112, having symmetrical leading and trailing tapered edges is such that the level of torque necessary to rotationally insert and secure anchor 102 in cortical bone or remove anchor 102 is greater than that commonly employed for other rotational fixation devices and provided by a commonly used orthopedic screwdriver. Commonly used fixation devices such as bone screws often slightly dislodge after a period of time from their embedded position for reasons described above and will be further discussed below and are easily removed requiring a very small level of torque.

Hence, unlike other devices, use of an orthopedic screwdriver may not be suffice to provide the necessary level of torque and an anchor driving tool in the form of a ratcheting socket wrench-type device (604, FIG. 6) may be required in order to secure anchor 102 in cortical bone. Once anchor 102 having symmetrical leading and trailing tapered edges is secured in place and following a period of bone healing, the level of torque required to loosen and dislodge anchor 102 can be even greater than that required to initially secure anchor 102 in place. This design provides a safety feature that enables only deliberate loosening of anchor 102 and prevents independent unintended loosening or axial pullout of anchor 102 and of an implant (e.g., 302, FIG. 3) fixated to bone by anchor 102.

In order to enable application of the greater level of torque necessary to secure anchor 102 in bone and as shown in FIG. 1A, system 100 also includes inserter 104, designed to adapt head 110 to accept an anchor driving tool in a form of a ratcheting socket wrench-type-device (604, FIG. 6). Inserter 104 can be geometrically shaped in a form of a polygon such as, for example, a hexagon, a square, a star and similar so that to fit inside any ratcheting socket wrench-type-type device head.

Inserter 104 can also include two or more driving pins 132 operative to be inserted into corresponding two or more smooth-walled bores 130 in head 110 and a through-hole 134 operative to accommodate locking screw 106 locking inserter 104 against surface 126 of head 110. Once anchor 102 is secured in bone, locking-screw 106 and inserter 104 can be removed and reused or discarded.

Figure 3:
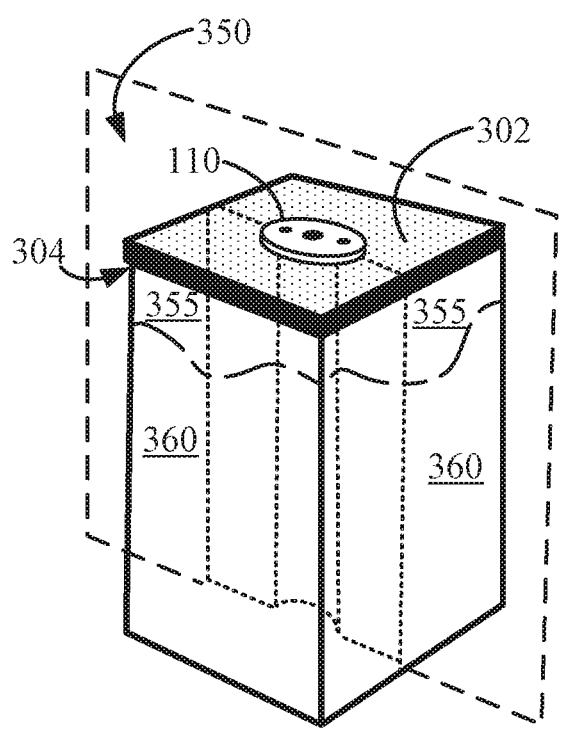
FIG. 3 is a perspective view and partial cross-section view simplified illustration of a universal system for fixation of implants to bone anchor in situ in accordance with still another example.

Reference is now made to FIG. 3, which is a perspective view simplified illustration of an example of a universal system for fixation of implants to bone anchor in situ, anchoring a fixation device to a sample of cortical 355 and cancellous 360 bone. As shown in FIG. 3, a plate 302, simulating an orthopedic fixation device, such as for example an arthroplasty implant, is fixated and pressed against a surface 304 of a cortical bone 355 layer of a bone sample by anchor 102 head 110. Plane 350 delineated by phantom lines defines a plane along which a cut is made in the sample cortical bone for purposes of illustration to provide the cutaway views depicted in FIGS. 4A-4C.

Figure 4A:
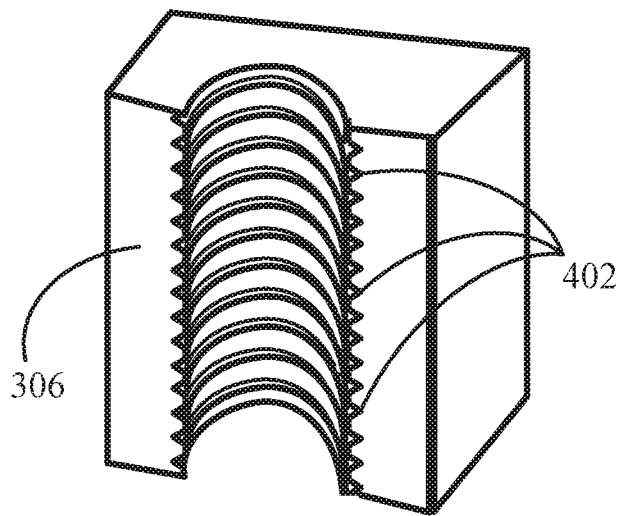
FIGS. 4A, 4B and 4C are perspective view simplified cutaway illustrations of fixation device imprints left in a sample of cortical bone in accordance with another example.
Figure 4B:
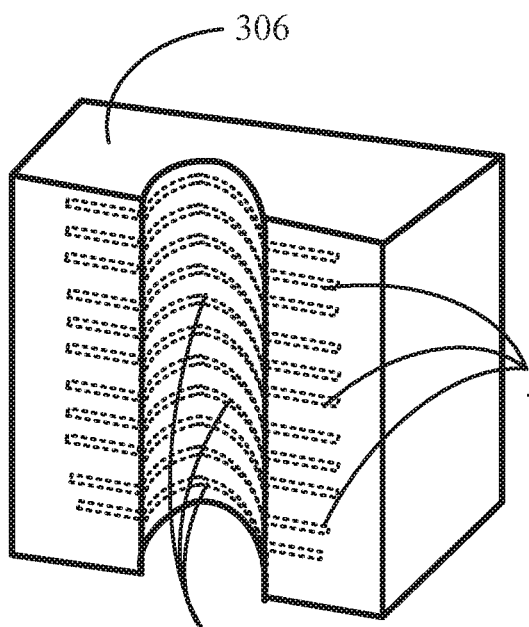
Figure 4C:
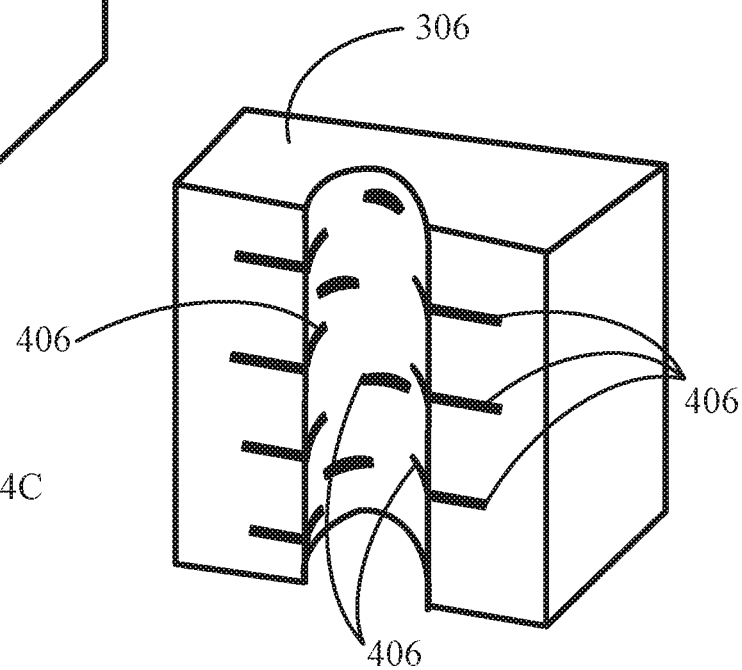

FIGS. 4A, 4B and 4C are cutaway view simplified illustrations of fixation device imprints left in a sample of cortical and/or cancellous bone by an embedded fixation/anchoring device. In FIGS. 4A-4C the fixation/anchoring device has been removed for clarity of explanation.

As can be appreciated from FIG. 4A, which is an imprint of an embedded commonly used cancellous bone screw (prior art), the bony thread made in the cortical bone is relatively shallow. In commonly used cortical bone screws the ratio between the screw shaft radius and the screw thread radius from the central longitudinal axis of the screw is commonly no greater than 1:1.66 which brings about a bony thread 402 cut out in cortical bone 304 by the screw thread that is shallow whereas the diameter of the bore accommodating the screw shaft is large. This design commonly brings about a risk of fixation device failure. Such failure commonly exhibits itself in the form of loosening, device fatigue and axial pull-out of the device, i.e., axial forces acting, for example on a screw and translated into rotational forces that cause the device to unscrew, loosen and dislodge bringing about irreversible loss of the bone-implant interface. Since the thread created in the bone cortex by the commonly used screws, as depicted in FIG. 4A, is relatively shallow, in some cases the bony thread itself may strip and the fixating device can lose its holding power or grip.

It will be appreciated that the bony thread carved by initial tapping of the bone prior to insertion of commonly used bone screws remains the same over time hence the level of torque necessary to remove such a screw is commonly the same or in some cases due to fixation device failure less than the level of torque necessary to insert the screw initially.

FIG. 4B is a cutaway view simplified illustration of an imprint of a universal system 100 for fixation of implants to bone anchor 102 immediately following anchoring. As anchor 102 is rotated against cortical bone, employing inserter 104 and a ratcheting socket wrench-type device 604 (FIG. 6), fins 112 cut a relatively deep helical groove 404 in untapped cortical bone 304. The proportional dimensions of anchor 102 and the ratio between the radius of anchor 102 shaft 108 and the radius of fins 112 from the central longitudinal axis (W) (FIG. 1) of anchor 102 is commonly greater than 1:1.66 which brings about firm stabilization of anchor 102 securing anchor 102 in place. This ratio also allows for a pre-drilled bore designed to accommodate anchor 102 shaft 108 to have a smaller radius than that required for standard orthopedic cortical bone screws maintaining bone structural strength at the location of fixation.

FIG. 4C, which is a cutaway view simplified illustration of an imprint of an embedded universal system 100 for fixation of implants to bone anchor 102 following a period of bone-healing and osseous integration, depicts growth of the boney cortex into helical groove 404 (FIG. 4B) except in slots 406 still occupied by fins 112. At the end of the osseous integration and healing period, fins 112 remain firmly inserted in slots 406 created by the now healed bone.

Removal of anchor 102 from its anchored location requires application of torque even greater than that applied during insertion of same anchor 102. During insertion, some fins 112 rotate outside the bone and once inserted, follow the helical groove already created by preceding fins 112. During extraction, each and every fin 112 meets great resistance by surrounding healed bone and needs to cut a new path for itself in the bone. Only following at least one full anti-clockwise rotation of anchor 102 does the level of resistance drop and the level of torque required becomes similar to that applied during insertion. The initial amount of torque required to loosen and dislodge anchor 102 from its secured location is greater than that provided by a commonly used screwdriver and requires employment of a ratcheting socket wrench-type device (604, FIG. 6).

Hence, in most cases, fixation of an implant to bone employing universal system 100 can be considered permanent or long-term fixation. System 100 can be commonly selected for procedures in which removal of the implant is not required or desired over a significant period of time such as in arthroplasty procedures, orthodontic procedures, carpal procedures and similar.

This design provides a safety feature that enables only deliberate loosening of anchor 102 and prevents independent unintended loosening or axial pullout of anchor 102 and of an implant (302, FIG. 3) fixated to bone by anchor 102.

Reference is now made to FIGS. 5A and 5B, together referred to as FIG. 5, which are perspective and partial cross section view simplified illustration of an implementation of a universal system for fixation of implants to bone in accordance with another example. Anchor 102 can be scaled down in size so that to be employed as an orthodontic anchor in orthodontic procedures to support orthodontic prostheses such as orthodontic abutment 506, bridges, dentures and crowns. In this configuration, anchor 112 can be rendered an orthodontic permanent implant. As shown in FIG. 5, anchor 102 is anchored and secured in bone of the jaw such as a mandibular bone 502 covered by gum tissue 504. Abutment 506 is shown in FIG. 5 to be attached to anchor 102 by a screw screwed into threaded bore 128 (FIG. 1) depicted in FIG. 5 by phantom lines. Threaded bore 128 is also operative to accommodate a temporary plug to prevent growth of tissue into bore 128 when anchor 102 is buried during a bone healing period.

In this configuration, universal system 100 for fixation of implants to bone is rendered mutatis mutandis an orthodontic insert system.

FIG. 6, which is a perspective partial cross-section view simplified illustration of an implementation of a universal system for fixation of implants to bone in accordance with yet another example, depicts universal system 100 for fixation of implants to bone anchor 102 partially embedded in cortical bone 602. In this example, inserter 104 is elongated to allow for better access to anchor 102 by a user. An anchor 102 driving tool 604, which is in the form of a ratcheting socket wrench-type device is employed to grip inserter 104, which is attached to head 110 and locked in place by locking screw 106. Driving tool 604 can be employed both for insertion and securing of anchor 102 in bone as well as for loosening and dislodging anchor 102 if desired. Once anchor 102 is secure in bone, inserter 104 and locking screw 106 can be removed and discarded or reused as desired.

The ratcheting mechanism of driving tool 604 can be unidirectional and irreversible including an internal fitting socket 606. Driving tool 604 can be employed to reverse the rotational direction of anchor 102 by removing driving tool 604, flipping driving tool 604 over as indicated by an arrow designated reference numeral 650 and reattaching tool 604 to inserter 104.

In orthodontic procedures described above and depicted in FIG. 5, once anchor 102 is secured in bone inserter 104 and locking screw 106 can be removed and discarded or reused as desired and replaced by an abutment-type device (506, FIG. 5) screwed into threaded bore 128 (FIGS. 1 and 5).

As shown in FIG. 5B, head 110 of anchor 102 intended for orthodontic procedures can also include a removable plug 508 so that to prevent tissue growth into threaded bore 128.

Figure 7A:
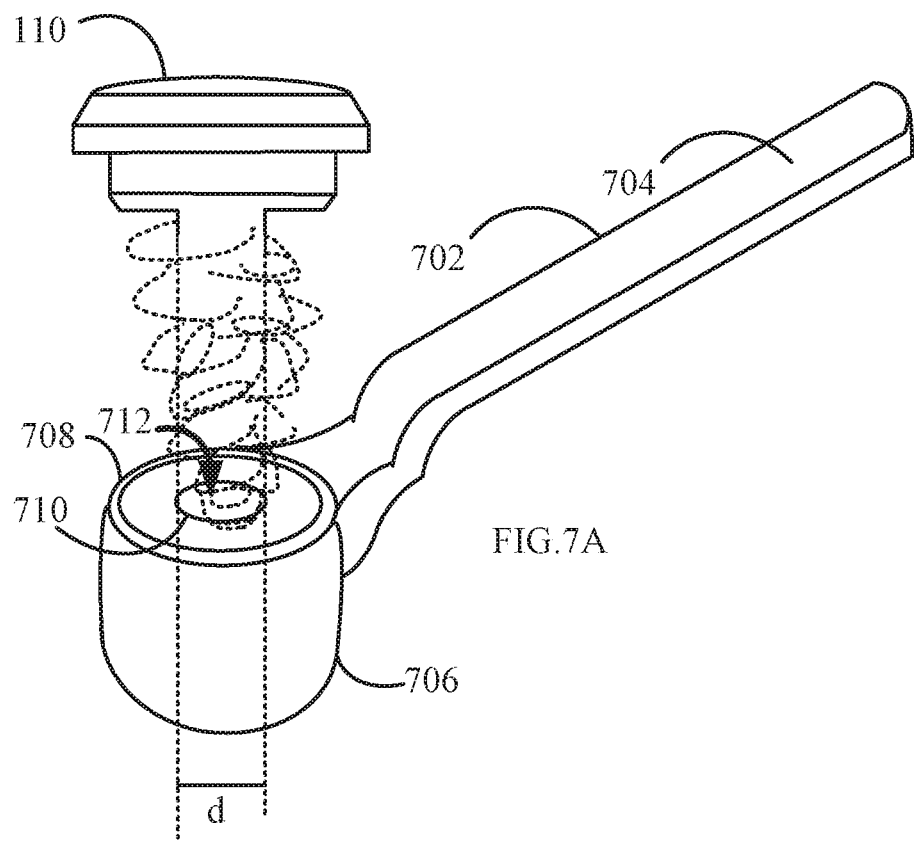
FIGS. 7A, 7B and 7C are perspective view and cross-section view simplified illustrations of a drill guide and implementation of a drill guide for a universal system for fixation of implants to bone in accordance with another example.
Figure 7C:
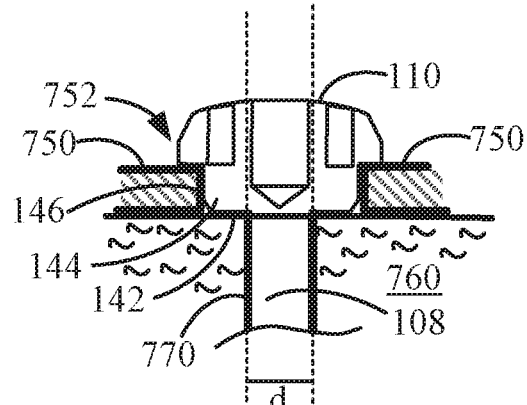
Figure 7B:
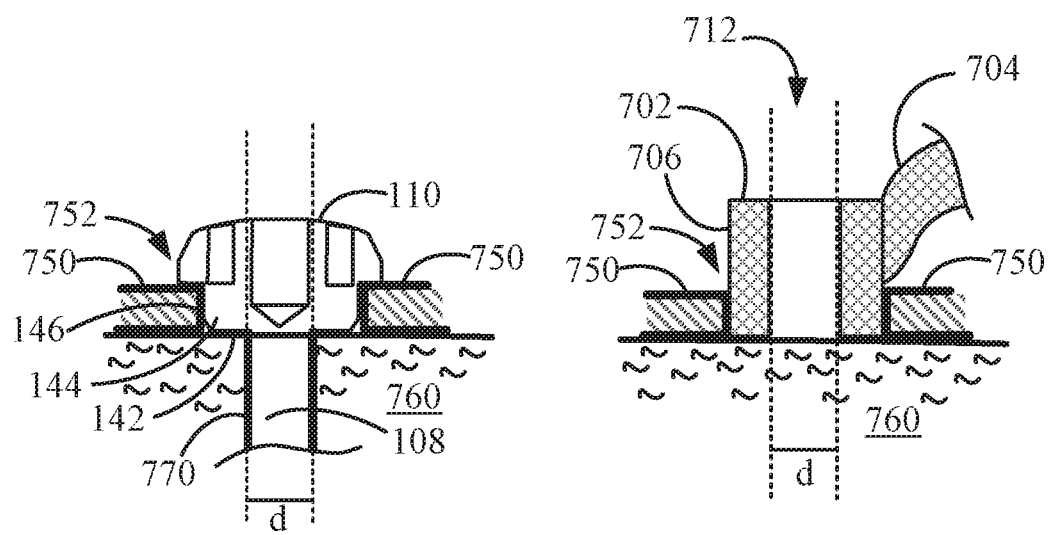

Reference is now made to FIGS. 7A, 7B and 7C, which are perspective view and cross-section view simplified illustrations of a drill guide for a universal system for fixation of implants to bone in accordance with another example. In FIG. 7A, shaft 108 and fins 112 are marked by phantom lines and in FIG. 7C fins 112 have been removed for clarity of explanation.

Commonly used drill guides in orthopedic and orthodontic medicine are designed to provide guidance for a shaft of a rotational fixation device such as a screw shaft. As explained above, unlike the commonly used fixation devices, anchor 102 includes a shoulder 144. A guide 702 can have a handle 704 and a guide sleeve 706 designed to have an external wall 708 and an internal wall 710 providing a guide hole 712. Guide hole 712 can have a diameter (d) equal to the diameter of corresponding shaft 108 so that to enable drilling a bore 770 to accommodate shaft 108. When inserted, shaft 108 can be accommodated by the drilled bore 770 whereas shoulder 144 can come to snugly rest in screw-hole 752. Optionally, a driving tool 704 can be of any shape and can be sufficiently narrow to fit between two teeth flanking to a missing tooth to be treated. Additionally and optionally, driving tool 704 could also include a protruding stabilizing shelf (not shown) positioned between driver handle 702 and driver wall 708 (FIG. 7A) protruding towards and along a buccal and/or lingual gingival surface of a dental arcade on which driving tool 704 is placed, parallel to guide hole 712 and operative to be urged against the dental arcade surface so that to stabilize the driver guide when drilling a hole into the jaw bone.

Referring now to FIGS. 7B and 7C, which are cross-section view simplified illustrations of implementation of a drill guide for a drill guide for a universal system for fixation of implants to bone in accordance with another example. An implant 750, for example a joint spacer such as that depicted in U.S. Pat. No. 8,403,985 commonly includes screw-holes 752 operative to accommodate fasteners or fixation devices such nails, pins, screws, sutures or staples. External wall 708 of sleeve 706 can have a diameter corresponding to the diameter of screw hole 752 so that to be snugly accommodated by screw hole 752 as illustrated in FIG. 7B.

Drill guide 702 sleeve 706 can be placed inside screw hole against the surface of bone 760 and a bore 770 is drilled through guide hole 712 to accommodate anchor 102 shaft 108. Drill guide 702 is then removed and anchor 102 inserted, shaft 108 guided by the bore 770 drilled through guide hole 712. Once fully inserted and secured in place, as illustrated in FIG. 7C, shoulder 144 of anchor 102 head 110 can be snugly accommodated in screw hole 752. The square angle between shoulder 144 wall 146 and base 142 prevents pendulous movement (rocking) of anchor 102 under forces of stress explained above, loosening and failure of fixation.

It will be appreciated by persons skilled in the art that the present method and system are not limited to what has been particularly shown and described hereinabove. Rather, the scope of the system and devices includes both combinations and sub-combinations of various features described hereinabove as well as modifications and variations thereof which would occur to a person skilled in the art upon reading the foregoing description and which are not in the prior art.

The invention claimed is:

1. An implant-to-bone anchor, comprising:
a shaft terminated at one end by a head including a shoulder having one or more walls parallel to a longitudinal axis of said shaft and disposed between a shaft-facing surface of said head and said shaft; and
a plurality of generally planar fins each comprising a major radius, a minor radius, a first surface, a second surface and a free edge corresponding to the major radius of each respective generally planar fin and having a beveled cross-section including a leading cutting-edge portion and a trailing cutting-edge portion;
wherein each of said plurality of generally planar fins are attached to said shaft along less than one half of a circumference of said shaft and angled about the minor radius thereof along an imaginary helix spiraling axially about said shaft such that each 360 degree rotation of the imaginary helix comprises only one of the plurality of generally planar fins,
wherein each of said plurality of generally planar fins are placed only partially above or partially under an adjacent generally planar fin,
and
wherein said minor radius of a generally planar fin of said plurality of generally planar fins which is located closest to said head is the largest in size and wherein said minor radius of a generally planar fin of said plurality of generally planar fins which is located farthest from said head is the smallest in size.

2. The anchor of claim 1, wherein each of said plurality of generally planar fins are attached to the shaft along between one third and one half of the circumference of the shaft.

3. The anchor of claim 1, wherein at least one of said plurality of generally planar fins at least partially overlaps at least one adjacent generally planar fin of said plurality of generally planar fins.

4. The anchor of claim 1, wherein a surface area of at least one of the first and second surfaces is between 1 and 1.5 times a surface area of a cross: section of the shaft.

5. The anchor of claim 1, wherein a surface area of at least one of the first and second surfaces is 1.5 times a surface area of a cross-section of the shaft.

6. The anchor of claim 1, wherein a maximum diameter of at least one of said plurality of generally planar fins is between 1.5 to 1.7 times a maximum diameter of the shaft.

7. The anchor of claim 1, wherein a maximum diameter of at least one of said plurality of generally planar fins is 1.7 times a maximum diameter of the shaft.

8. The anchor of claim 1, wherein at least one of the plurality of generally planar fins is attached to both said shoulder and said shaft.

9. The anchor of claim 1, wherein at least one of the plurality of generally planar fins is positioned along the shaft at a distance between 2-3 mm from said shoulder.

10. The anchor of claim 1, wherein the shoulder is configured to be snugly received in a screw hole of an implant when the anchor is fully inserted and secured in place.

11. The anchor of claim 1, wherein said first and second surfaces come together at said trailing cutting-edge portion of said free edge.

* * * * *